United States Patent [19]
Huang et al.

(12) United States Patent
Huang et al.

(10) Patent No.: US 8,784,912 B2
(45) Date of Patent: Jul. 22, 2014

(54) FERMENTED COMPOSITION OF MUNG BEAN HULLS, METHOD FOR FORMING THEREOF, AND ANTI-OXIDATION AND ANTI-INFLAMMATION COMPOSITION USING THE SAME

(75) Inventors: Shu-Chen Huang, Hsinchu (TW);
Hing-Yuen Chan, Hsinchu (TW);
Chiao-Ming Liao, Hsinchu (TW);
Li-Chuan Liao, Hsinchu (TW);
Shiaw-Min Hwang, Hsinchu (TW)

(73) Assignee: Food Industry Research & Development Institute, Hsinchu (TW)

( * ) Notice: Subject to any disclaimer, the term of this patent is extended or adjusted under 35 U.S.C. 154(b) by 574 days.

(21) Appl. No.: 12/581,266

(22) Filed: Oct. 19, 2009

(65) Prior Publication Data
US 2011/0038969 A1    Feb. 17, 2011

(30) Foreign Application Priority Data

Aug. 11, 2009   (TW) ............................... 98126915 A

(51) Int. Cl.
*A61K 36/00*  (2006.01)
*A23L 1/20*   (2006.01)
*A61K 36/06*  (2006.01)
*A61K 36/48*  (2006.01)
*A61K 36/062* (2006.01)
*A23L 1/30*   (2006.01)

(52) U.S. Cl.
CPC ............ *A61K 36/062* (2013.01); *A23L 1/3002* (2013.01); *A23L 1/3016* (2013.01); *A61K 36/48* (2013.01)
USPC ...... 424/776; 424/195.15; 424/757; 424/725; 426/46

(58) Field of Classification Search
None
See application file for complete search history.

(56) References Cited

U.S. PATENT DOCUMENTS

2009/0068150 A1    3/2009   Park et al.

FOREIGN PATENT DOCUMENTS

| CN | 1042053 | 5/1990 |
| CN | 1062275 | 7/1992 |
| CN | 1188610 | 7/1998 |
| CN | 1309932 | 8/2001 |
| CN | 1385192 | 12/2002 |
| TW | 200638877 | 11/2006 |
| TW | 200745338 | 10/2009 |

OTHER PUBLICATIONS

Chou et al. (2008) Intern. J. Food Science and Tech. 43, 1371-1378.*
Esaki et al. (1997) J. Agric. Food Chem. 45, 2020-2024.*
Randhir et al. (2007) Innovative Food Science and Emerging Technologies 8, 197-204.*
Duh et al. (1999) Food and Chemical Toxicology 37, 1055-1061.*
English abstract of CN1042053, pub. May 16, 1990.
English abstract of CN1062275, pub. Jul. 1, 1992.
English abstract of CN1188610, pub. Jul. 29, 1998.
English abstract of CN1309932, pub. Aug. 29, 2001.
English abstract of CN1385192, pub. Dec. 18, 2002.
English abstract of TW200638877, pub. Nov. 16, 2006.
English abstract of TW200745338, pub. Dec. 16, 2007.
"Anti-inflammatory and related pharmacological activities of cultured mycelia and fruiting bodies of *Cordyceps militaris*" So Young Won et al., Journal of Ethnopharmacology 96 (2005) 555-561.
"Antioxidative Properties of Xanthan on the Autoxidation of Soybean Oil in Cyclodextrin Emulsion" Kazuko Shimada et al., J. Agric. Food Chem. 1992, 40, 945-948.
"Chemical Composition and Antioxidant Activity of Seeds of Different Cultivars of Mungbean" R. Anwar et al., JFS Sensory and Nutritive Qualities of Food, vol. 72, Nr. 7, 2007 Journal of Food Science.
"In vitro anti-inflammatory and anti-oxidative effects of *Cinnamomum camphora* extracts" Hye Ja Lee et al., Journal of Ethnopharmacology 103 (2006) 208-216.
Bacterial Strains BERC 31200, BCRC32286 and BCRC33070 which showed in the specification have been deposited in German DSMZ on Sep. 30, 2009 (DSMZ is a qualified deposition organization under Budapest Treaty since Oct. 1, 1981). The deposition Nos. are DSM23003, DSM23004 and DSM23005. Strains utilized in the specification are commercial available from the deposition center which anyone can order any of the strains.

* cited by examiner

*Primary Examiner* — Chris R Tate
*Assistant Examiner* — Russell Fiebig
(74) *Attorney, Agent, or Firm* — McClure, Qualey & Rodack, LLP

(57) ABSTRACT

The invention provides a method for forming a fermented composition of mung bean hulls, including: mixing mung bean hulls and water to form a mixture; adding a fungus into the mixture, wherein the fungus includes *Rhizopus* spp. or *Aspergillus* spp.; and fermenting the mixture to form a fermented composition. The invention also includes a fermented composition of mung bean hulls by the method and an anti-oxidation and anti-inflammation composition containing the fermented composition of mung bean hulls.

25 Claims, No Drawings

FERMENTED COMPOSITION OF MUNG BEAN HULLS, METHOD FOR FORMING THEREOF, AND ANTI-OXIDATION AND ANTI-INFLAMMATION COMPOSITION USING THE SAME

CROSS REFERENCE TO RELATED APPLICATIONS

This Application claims priority of Taiwan Patent Application No. 098126915, filed on Aug. 11, 2009, the entirety of which is incorporated by reference herein.

BACKGROUND OF THE INVENTION

1. Field of the Invention

The present invention relates to a fermented composition and method for forming thereof, and in particular relates to a fermented composition of mung bean hulls, method for forming thereof, wherein the fermented composition of mung bean hulls has anti-oxidation and anti-inflammation effects.

2. Description of the Related Art

Mung bean products mainly comprise mung beans without hulls, germinated mung beans and mung bean soup. Specific types of mung beans comprise defensins that inhibit inflammation through inhibiting nitric oxide production. Moreover, it was reported that mung bean soup has anti-oxidation effects. Note that numerous patents for applying mung bean have been disclosed.

Taiwan patent publication number 200745338 discloses a method for manufacturing enzyme of mung bean fermented with *Antrodia camphorate*, which comprise re-fermenting the fermented product of entire mung bean with *Antrodia camphorate*, and then after drying and grinding, filling the fermented product into capsules or tableting the fermented product. The enzyme of mung bean fermented with *Antrodia camphorate* has anti-viral and chemical toxin dissolution effects, among others.

US patent publication number 2009/0068150 A1 discloses an extract, wherein mung beans are washed with water and then extracted. Then, after the extract is sterilized, a lactic acid bacteria is added therein for fermentation. Next, after isolation, a formula is added therein for cosmetic product applications.

During manufacturing of mung bean products having mung beans without hulls, mung bean hulls are removed. Currently, the removed mung bean hulls are not recycled into food products or food by-products (such as a fermented product thereof).

BRIEF SUMMARY OF THE INVENTION

The invention provides a method for forming a fermented composition of mung bean hulls, comprising: mixing mung bean hulls and water to form a mixture; adding a fungus into the mixture, wherein the fungus comprises *Rhizopus* spp. or *Aspergillus* spp.; and fermenting the mixture to form a fermented composition.

The invention also provides a fermented composition of mung bean hulls having anti-oxidation and anti-inflammation effects, formed by a method comprising the following steps: mixing mung bean hulls and water to form a mixture; adding a fungus into the mixture, wherein the fungus comprises *Rhizopus* spp. or *Aspergillus* spp.; and fermenting the mixture to form a fermented composition.

The invention further provides an anti-oxidation and anti-inflammation composition, comprising: an effective amount of the fermented composition of mung bean hulls as mentioned above; and a pharmaceutically acceptable salt or carrier.

A detailed description is given in the following embodiments with reference to the accompanying drawings.

BRIEF DESCRIPTION OF THE DRAWINGS

None

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The bacterial strains, *Aspergillus sojae* BCRC 31200, *Aspergillus oryzae* var. *oryzae* BCRC 32286 and *Rhizopus oryzae* BCRC33070 in the following description have been deposited with Deutsche Sammlung von Mikroorganismen and Zellkulturen GmbH (DSMZ) (German Collection of Microorganisms and Cell Cultures) at Sep. 30, 2009 and have been assigned the accession numbers DSM 23003, DSM 23004 and DSM 23005, respectively.

A method for forming a fermented composition of mung bean hulls of the invention will be detailed in the following.

First, mung bean hulls and water are mixed well to form a mixture. In the invention, the mung bean hulls are not limited to being from a specific type of mung beans. In one embodiment, the mung bean hulls may be from mung beans Taiwan No. 5, mung beans Taiwan No. 3 or the combination thereof. Further, a ratio of the mung bean hulls to water may be about 0.1-3:4-5. In one embodiment, a ratio of the mung bean hulls to water may be about 3:5.

Next, after the mixture is sterilized, an activated fungus is added into the mixture to perform inoculation. An activated spore solution of the fungus with a concentration of about $10^6$-$10^{10}$ CFU/ml may be inoculated into the mixture and a ratio of the activated spore solution and the mixture may be about 1-50 (v/w).

The fungus may comprise *Rhizopus* spp. or *Aspergillus* spp. *Rhizopus* spp. may comprise *Rhizopus oryzae* and in one embodiment, *Rhizopus oryzae* may comprise *Rhizopus oryzae* BCRC33070 (DSM 23005). *Aspergillus* spp. may comprise *Aspergillus sojae* or *Aspergillus oryzae* var. *oryzae*. *Aspergillus sojae* may comprise *Aspergillus sojae* BCRC 31200 (DSM 23003) and *Aspergillus oryzae* var. *oryzae* may comprise *Aspergillus oryzae* var. *oryzae* BCRC 32286 (DSM 23004). The BCRC numbered strains mentioned above all may be bought from the Food Industry Research and Development Institute (FIRDI) (331 Shih-Pin Road, Hsinchu, 300 Taiwan R.O.C.), and are also deposited under the Budapest Treaty in the Deutshe Sammlung von Mikroorganismen and Zellkulturen GmBH (DSMZ), Inhoffenstr. 7B, D-38124 Braunschweig, Germany as DSM 23003, DSM23004, and DSM23005, respectively; the deposits will be maintained under the terms of the Budapest Treaty on the International Recognition of the Deposit of Microorganisms and are freely available to the public).

The steps of activating the fungus and adding the activated fungus to the mixture mentioned above are described in the following.

First, lyophilized spore powder is added into sterilized water. After the lyophilized spore powder is dissolved, the spore suspension is piped with a sterilized pipette and dropped into a tube containing sterilized water and then the tube is vortexed to mix the spore solution and the sterilized water well to form a fungus suspension. An appropriate amount of the fungus suspension is applied on a plate at 20-32° C., and after being cultured for 5-15 days, is transferred to a new plate to complete activation of the fungus. In one embodiment, the plate may comprise a potato dextrose agar (PDA) plate.

An appropriate amount of sterilized water is added to the plate with activated fungus mentioned above and spores thereon are scraped by a loop to form a spore suspension. An appropriate amount of the spore suspension (with a concentration of about $10^6$-$10^{10}$ CFU/ml) is inoculated into the sterilized mixture mentioned above (as a substrate) and mixed well to complete inoculation.

Then, after the activated fungus is added into the mixture, a fermentation process is performed to the mixture to form a fermented composition. According to the condition of the mixture, the fermentation may be liquid or solid-state fermentation. In one embodiment, the form of the fermentation may be a solid state fermentation. A temperature for the fermentation may be about 20-32° C., and in one embodiment, a temperature for the fermentation may be 25° C. A time for the fermentation may be about 5-15 days, and in one embodiment, a time for the fermentation may be 7 days. After the fermentation is completed, the obtained fermented composition is the fermented composition of mung bean hulls of the invention.

Furthermore, the fermented composition of mung bean hulls of the invention may be further lyophilized to form a lyophilized fermented composition and the lyophilized fermented composition may be extracted with a solvent. In one embodiment, the solvent may comprise water. A ratio of the lyophilized fermented composition to the solvent may be about 1-2:5-15 (w/v) and in one embodiment, may be about 1:10 (w/v). A temperature of the extraction may be 7-70° C., and in one embodiment, may be about 70° C. Moreover, time for extraction may be 1-24 hours, and in one embodiment, may be about 1 hour.

By applying the method for determining 2,2-diphenyl-1-picrylhydrazyl (DPPH) free radical-scavenging ability described in Shimada et al (1992)(J. Agric. Food Chem 40: 945-948) and the method for determining nitric oxide inhibition ability described in Won (2005)(J. of Ethnopharmacology 96 (2005) 551-561) and Lee(2006)(J. of Ethnopharmacology 103 (2006) 208-216) to the fermented composition of mung bean hulls of the invention, anti-oxidation and anti-inflammation effects, respectively, of the fermented composition of mung bean hulls of the invention may be determined.

A 2,2-diphenyl-1-picrylhydrazyl (DPPH) free radical-scavenging rate of the fermented composition of mung bean hulls of the invention may be about 21-48%, and is preferably 48%. A nitric oxide inhibition rate of the fermented composition of mung bean hulls of the invention is about 12-32%, and is preferably 32%.

In addition, the invention may further comprise an anti-oxidation and anti-inflammation composition which comprises an effective amount of the fermented composition of mung bean hulls as mentioned above and a pharmaceutically acceptable carrier or salt.

A pharmaceutically acceptable carrier may comprise, but is not limited to, a solvent, a dispersion medium, a coating, an antibacterial and antifungal agent, or an isotonic and absorption delaying agent. The pharmaceutical composition can be formulated into dosage forms for different administrative routes utilizing conventional methods.

The pharmaceutically acceptable salt may comprise, but is not limited to, inorganic cation salts including alkali metal salts such as sodium salt, potassium salt or amine salt, alkaline-earth metal salt such as magnesium salt or calcium salt, the salt containing bivalent or quadrivalent cation such as zinc salt, aluminum salt or zirconium salt. In addition, the pharmaceutically acceptable salt may also comprise organic salt including dicyclohexylamine salt, methyl-D-glucamine, and amino acid salt such as arginine, lysine, histidine, or glutamine.

The pharmaceutical composition may be administered orally, parentally by an inhalation spray or via an implanted reservoir. The parental method may comprise subcutaneous, intracutaneous, intravenous, intramuscular, intraarticular, intraarterial, intrasynovial, intrasternal, intrathecal, and intralesional, as well as infusion techniques.

An oral composition can comprise, but is not limited to, tablets, capsules, emulsions and aqueous suspensions, dispersions and solutions.

EXAMPLE

The BCRC numbered strains used in the examples may all be bought from the Food Industry Research and Development Institute (FIRDI) (331 Shih-Pin Road, Hsinchu, 300 Taiwan R.O.C.).

Example 1

1. Fungus Culturing
(1) Strain Selection 4 strains of *Rhizopus*, 2 strains of *Aspergillus*, 3 strains of *Actinomucor* and 1 strain of lactic acid bacteria were obtained from the Food Industry Research and Development Institute (FIRDI), as shown in Table 1.

(2) Activating the Fungus

A cotton ball with 70% ethanol was used to wipe the outer tube of a lyophilized spore tube and the tip of the outer tube was heated by fire. Several drops of sterilized water were dropped on the heated position of the outer tube to make the outer tube crack and subsequently break. The heat insulating cellulose paper and the inner tube of the spore tube were taken out of the spore tube and a cotton stopper of the inner tube was taken off the inner tube by a sterilized tweezer. 0.3-0.5 ml of sterilized water was drop-by-drop piped by a sterilized pipette to the inner tube. After the powder in the inner tube was dissolved in the sterilized water, the sterilized water containing the powder was drop-by-drop piped by a sterilized pipette into another tube containing 5 ml of sterilized water. The tube was next vortexed, for complete mixing, to form a fungus suspension. Then, 0.1-0.2 ml of the fungus suspension was applied on the potato dextrose agar (PDA) plate at a temperature of 20-32° C., and after being cultured for 7 days, was transferred to a new potato dextrose agar (PDA) plate to complete activation of the fungus.

(3) Substrate Treatment Before Fermentation

About 50 g of mung bean hulls was placed in a glass bottle (diameter: 9 cm; height: 10 cm) and added 15 ml of distilled water. Then, the mung bean hulls and distilled water were well mixed and sterilized at 121, 1.2 Kg/cm² for 20 minutes.

(4) Solid State Fermentation

An appropriate amount of sterilized water was added to the cultured potato dextrose agar (PDA) plate with respective activated fungus and then the spores thereon were scraped by a loop to form a spore suspension. 1 ml of the spore suspension was inoculated into the sterilized substrate, well mixed and cultured in the incubator at a temperature of 25° C. for 7 days.

2. Lyophilization

After the fermentation was completed, the product therefrom was lyophilized.

3. Extraction of the Fermentation Product

The respective fermented substrate of mung bean hulls was shattered. 5 g of the sample fermented with the respective fungus was added into 50 ml of distilled water (a ratio of solid to liquid was 1:10) and extracted at a temperature of 70° C. for 1 hour. After the extraction was completed, suction filtration was performed to obtain the water extract of the sample fermented with respective fungus. The water extract was placed in a refrigerator at a temperature of −20° C. for freezing and use in effect analysis.

4. Effect Estimate of the Fermentation Product (1) Anti-oxidation effect (Determination of 2,2-diphenyl-1-picrylhydrazyl (DPPH) free radical-scavenging ability)

According to the method described in Shimada et al (1992) (J. Agric. Food Chem 40: 945-948), trolox was used as a standard sample to produce a standard curve of 2,2-diphenyl-1-picrylhydrazyl (DPPH) free radical-scavenging ability. 50 ml of trolox with different concentrations were added to 150 μl of a fresh prepared solution of 0.4 mM 2,2-diphenyl-1-picrylhydrazyl (DPPH) in methanol, respectively and mixed well. After placed for 90 minutes, the absorbance at 517 nm of the trolox with different concentrations added with the solution of 2,2-diphenyl-1-picrylhydrazyl (DPPH) in methanol were determined, respectively to determined the 2,2-diphenyl-1-picrylhydrazyl (DPPH) free radical-scavenging abilities of trolox at different concentrations, producing a standard curve thereof.

After each water extract sample was treated with the same condition, absorbance at 517 nm thereof was determined, respectively and compared with the standard curve to calculate the 2,2-diphenyl-1-picrylhydrazyl (DPPH) free radical-scavenging ability of each sample (present by μmol trolox/g sample). The lower the absorbance was, the stronger the 2,2-diphenyl-1-picrylhydrazyl (DPPH) free radical-scavenging ability of the sample was. The 2,2-diphenyl-1-picrylhydrazyl (DPPH) free radical-scavenging ability of each sample is shown in Table 1.

(2) Anti-Inflammation (In Vitro Inhibiting Nitric Oxide Test)

(a) Cell Culturing

The method described in Won (2005)(J. of Ethnopharmacology 96 (2005) 551-561) and Lee(2006)(J. of Ethnopharmacology 103 (2006) 208-216) was used as a template. A cell line RAW 264.7 (BCRC 60001, ATCC TIB-71), Mouse macrophage cell (provided from the Food Industry Research and Development Institute) was cultured with a DEME medium containing 10% fetal bovine serum and 2 mM L-glutamine at a temperature of 37° C. in a 5% $CO_2$ incubator.

(b) Analysis of Nitric Oxide

RAW 264.7 mouse macrophage cells in the medium were added to a 96 well plate (1×10$^5$ cells/well) and cultured over night. Then, 100 ng/ml lipopolysaccharide (LPS), 1 ng/ml interferon-γ (INF-γ) and water extract samples with different concentrations (1%, 5% and 10%) were added to the cells in medium and cultured for 24 hours. Next, 50 μl of the cell cultured medium was added to an another 96 well plate and 100 μl of Griess reagent which contained 50 μl of solution A (60 mM sulfanilamide) and 50 μl of solution B (4 mM 1N-1-naphtylethylenediamine) was added thereto. After, the cell cultured medium was vortexed for 5 minutes and absorbance at 540 nm thereof was determined by an immunofluorescence meter.

(c) Calculation 100 ng/ml lipopolysaccharide (LPS) and 1 ng/ml interferon-γ (INF-γ), used as a positive control, were added to cells in the medium. The nitric oxide production amount thereof was taken as 100%, and all other samples were compared with the positive control group. A lower percentage of nitric oxide production meant that the sample had inhibition ability for nitric oxide production, while a higher percentage of the nitric oxide production meant that the sample had promotional ability for nitric oxide production, i.e. promoting ability for immune response.

The inhibition ability for nitric oxide production of each sample is shown in Table 1.

5. Experiment Results 2,2-diphenyl-1-picrylhydrazyl (DPPH) free radical-scavenging rate and nitric oxide inhibition rate of the substrate before fermentation were 17% and 2%, respectively (see Table 1). After the substrate was fermented, the strains in *Rhizopus* which were able to increase the 2,2-diphenyl-1-picrylhydrazyl (DPPH) free radical-scavenging ability (2 times that of the control group) and nitric oxide inhibition ability (above 10 times that of the control group) of the substrate at the same time, only comprised *Rhizopus oryzae* BCRC33070 which had significant effects. All strains belonged to *Actinomucor* and the lactic acid bacteria had no effect for increasing 2,2-diphenyl-1-picrylhydrazyl (DPPH) free radical-scavenging ability and nitric oxide inhibition ability. Further, all of the test strains belonging to *Aspergillus* (BCRC 31200 and 32286) had significant effects for increasing 2,2-diphenyl-1-picrylhydrazyl (DPPH) free radical-scavenging ability and nitric oxide inhibition ability.

TABLE 1

2,2-diphenyl-1-picrylhydrazyl (DPPH) free radical-scavenging rate and nitric oxide inhibition rate of fermented compositions of mung bean hulls from respective strain

| BCRC No. | Strain | DPPH free radical-scavenging rate (%) | Time | NO inhibition rate (%) | Time |
|---|---|---|---|---|---|
| | Control group (before fermentation) | 17 | 1.0 | 2 | 1.0 |
| 32301 | *Rhizopus oryzae* | 32 | 1.9 | 16 | 8.0 |
| 33070 (DSM 23005) | *Rhizopus oryzae* | 40 | 2.4 | 20 | 10 |
| 33071 | *Rhizopus oryzae* | 38 | 2.2 | 12 | 6.0 |
| 31750 | *Rhizopus microsporus* var. *oligosporus* | 21 | 1.2 | 15 | 7.5 |
| 31200 (DSM 2303) | *Aspergillus sojae* | 48 | 2.8 | 32 | 16.0 |
| 32286 (DSM 23004) | *Aspergillus oryzae* var. *oryzae* | 42 | 2.4 | 22 | 11.0 |
| 31342 | *Actinomucor elegans* | 32 | 1.9 | 26 | 13.0 |
| 32967 | *Actinomucor taiwanensis* | 22 | 1.3 | 15 | 7.5 |
| 32669 | *Actinomucor taiwanensis* | 33 | 1.9 | 23 | 11.5 |
| 16000 | *Lactobacillus rhamnosus* | 20 | 1.2 | 18 | 9.0 |

Example 2

According the method used in example 1, another batch of mung bean hulls was fermented with the two strains of *Aspergillus*, respectively and the results were shown in Table 2. The 2,2-diphenyl-1-picrylhydrazyl (DPPH) free radical-scavenging rate and nitric oxide inhibition rate of the substrate before fermentation were 17% and 22.6%, respectively (Table 2). After the substrate was fermented, the 2,2-diphenyl-1-picrylhydrazyl (DPPH) free radical-scavenging ability and nitric oxide inhibition ability of the substrate were increased at the same time, wherein 2,2-diphenyl-1-picrylhydrazyl (DPPH) free radical-scavenging ability of the substrate was over 3 times that of the control group and nitric oxide inhibition ability of the substrate was over 2 times that of the control group. The results showed that the effects of different batches of mung bean hulls had significant differences. However, after fermented with microorganisms, antioxidation and anti-inflammation effects of the substrate all increased, significantly.

TABLE 2

2,2-diphenyl-1-picrylhydrazyl (DPPH) free radical-scavenging rate and nitric oxide inhibition rate of fermented compositions of mung bean hulls from *Aspergillus sojae* 31200 and *Aspergillus oryzae* var. *oryzae* 32286

| BCRC No. | Strain | DPPH free radical-scavenging rate (%) (Time) | NO inhibition rate (%) (Time) |
| --- | --- | --- | --- |
|  | Control group (before fermentation) | 17.0 ± 1.7 (1.0) | 22.6 ± 3.2 (1.0) |
| 31200 (DSM 23003) | *Aspergillus sojae* | 57.3 ± 5.9 (3.4) | 85.8 ± 2.9 (3.8) |
| 32286 (DSM 23004) | *Aspergillus oryzae* var. *oryzae* | 68.3 ± 7.5 (4.0) | 47.5 ± 2.9 (2.1) |

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for forming a fermented composition of mung bean hulls, comprising the steps of:
   (a) separating the hulls from the other parts of mung beans to obtain isolated mung bean hulls;
   (b) mixing the isolated mung bean hulls and water to form a mixture;
   (c) adding an effective amount of activated fungus into the mixture to ferment said mixture, wherein the activated fungus comprises *Rhizopus* spp. or *Aspergillus* spp.; and
   (d) incubating the mixture at 20-32° C. for 5-15 days to form the fermented mixture of mung bean hulls,
   wherein the method is a method for recycling removed mung bean hulls from manufacture of mung bean products having mung beans without hull, into food by-products.

2. The method for forming a fermented composition of mung bean hulls as claimed in claim 1, wherein the *Rhizopus* spp. comprises *Rhizopus oryzae*.

3. The method for forming a fermented composition of mung bean hulls as claimed in claim 2, wherein the *Rhizopus oryzae* comprises *Rhizopus oryzae* BCRC33070 (DSM 23005).

4. The method for forming a fermented composition of mung bean hulls as claimed in claim 1, wherein the *Aspergillus* spp. comprises *Aspergillus sojae* or *Aspergillus oryzae* var. *oryzae*.

5. The method for forming a fermented composition of mung bean hulls as claimed in claim 4, wherein the *Aspergillus sojae* comprises *Aspergillus sojae* BCRC 31200 (DSM 23003).

6. The method for forming a fermented composition of mung bean hulls as claimed in claim 4, wherein the *Aspergillus oryzae* var. *oryzae* comprises *Aspergillus oryzae* var. *oryzae* BCRC 32286 (DSM 23004).

7. The method for forming a fermented composition of mung bean hulls as claimed in claim 1, wherein a form of the fermented composition is a solid-state fermentation.

8. The method for forming a fermented composition of mung bean hulls as claimed in claim 1, further comprising lyophilizing the fermented composition to form a lyophilized fermented composition.

9. The method for forming a fermented composition of mung bean hulls as claimed in claim 8, further comprising extracting the lyophilized fermented composition with a solvent.

10. The method for forming a fermented composition of mung bean hulls as claimed in claim 9, wherein a ratio of the lyophilized fermented composition to the solvent is about 1-2:5-15 (w/v).

11. The method for forming a fermented composition of mung bean hulls as claimed in claim 9, wherein a temperature of the extracting is about 7-70° C.

12. The method for forming a fermented composition of mung bean hulls as claimed in claim 9, wherein a time for extracting the lyophilized fermented composition with a solvent is about 1-24 hours.

13. The method for forming a fermented composition of mung bean hulls as claimed in claim 9, wherein the solvent comprises water.

14. A fermented composition of mung bean hulls, having anti-oxidation and anti-inflammation effects, formed by a method comprising the following steps:
   (a) separating the hulls from the other parts of mung beans to obtain isolated munq bean hulls;
   (b) mixing the isolated mung bean hulls and water to form a mixture;
   (c) adding an effective amount of activated fungus into the mixture to ferment said mixture, wherein the activated fungus comprises *Rhizopus* spp. or *Aspergillus* spp.; and
   (d) incubating the mixture at 20-32° C. for 5-15 days to form the fermented mixture of munq bean hulls,
   wherein the fermented composition of mung bean hulls is a food by-product obtained from recycling removed munq bean hulls from manufacture of munq bean products having mung beans without hull.

15. The fermented composition of mung bean hulls as claimed in claim 14, wherein the *Rhizopus* spp. comprises *Rhizopus oryzae*.

16. The fermented composition of mung bean hulls as claimed in claim 15, wherein the *Rhizopus oryzae* comprises *Rhizopus oryzae* BCRC33070 (DSM 23005).

17. The fermented composition of mung bean hulls as claimed in claim 14, wherein the *Aspergillus* spp. comprises *Aspergillus sojae* or *Aspergillus oryzae* var. *oryzae*.

18. The fermented composition of mung bean hulls as claimed in claim 17, wherein the *Aspergillus sojae* comprises *Aspergillus sojae* BCRC 31200 (DSM 23003).

19. The fermented composition of mung bean hulls as claimed in claim 17, wherein the *Aspergillus oryzae* var. *oryzae* comprises *Aspergillus oryzae* var. *oryzae* BCRC 32286 (DSM 23004).

20. The fermented composition of mung bean hulls as claimed in claim 14, wherein a form of the fermented composition is a solid-state fermentation.

21. The fermented composition of mung bean hulls as claimed in claim 14, wherein a 2,2-diphenyl-1-picrylhydrazyl (DPPH) free radical-scavenging rate of the fermented composition is about 21-48%.

22. The fermented composition of mung bean hulls as claimed in claim 14, wherein a nitric oxide inhibition rate of the fermented composition is about 12-32%.

23. An anti-oxidation and anti-inflammation composition, comprising:
   an effective amount of the fermented composition of mung bean hulls as claimed in claim 14; and
   a pharmaceutically acceptable salt or carrier.

24. The anti-oxidation and anti-inflammation composition as claimed in claim 23, wherein a 2,2-diphenyl-1-picrylhydrazyl (DPPH) free radical-scavenging rate of the fermented composition is about 21-48%.

25. The anti-oxidation and anti-inflammation composition as claimed in claim 23, wherein a nitric oxide inhibition rate of the fermented composition is about 12-32%.

\* \* \* \* \*